United States Patent [19]

Rogler

[11] Patent Number: 5,469,844
[45] Date of Patent: Nov. 28, 1995

[54] MEDICAL MONITOR

[75] Inventor: Dietrich Rogler, Horb, Germany

[73] Assignee: Hewlett-Packard Company, Palo Alto, Calif.

[21] Appl. No.: 219,411

[22] Filed: Mar. 28, 1994

Related U.S. Application Data

[63] Continuation of Ser. No. 767,240, Sep. 27, 1991, abandoned.

[30] Foreign Application Priority Data

Oct. 26, 1990 [EP] European Pat. Off. ............ 90120519

[51] Int. Cl.⁶ .................................................. B65D 85/00
[52] U.S. Cl. ........................ 128/630; 206/305; 206/320; 206/363; 379/437; 379/438; 379/440
[58] Field of Search ............................. 128/630, 419 R; 361/392, 394, 395, 399, 428; 206/305, 320, 333, 316.1, 327, 328, 363; 379/435, 437, 438, 440

[56] References Cited

U.S. PATENT DOCUMENTS

| | | | |
|---|---|---|---|
| 1,066,280 | 7/1913 | Kaempfer | 206/333 |
| 1,240,239 | 9/1917 | Moffett | 206/333 |
| 3,621,844 | 3/1969 | Hayashi et al. | 128/2.05 |
| 3,994,283 | 11/1976 | Farley | 128/630 |
| 4,180,161 | 12/1979 | Henrickson et al. | 206/328 |
| 4,303,156 | 12/1981 | Vucich | 206/305 |
| 4,412,616 | 11/1983 | Williams | 206/333 |
| 4,458,813 | 7/1984 | Tushinsky et al. | 206/320 |
| 4,513,295 | 4/1985 | Jones et al. | 128/630 |
| 4,658,956 | 4/1987 | Takeda et al. | 206/305 |
| 4,718,085 | 1/1988 | Haskins | 379/438 |
| 4,821,150 | 4/1989 | Duthie et al. | 361/428 |
| 4,855,845 | 8/1989 | Thrush | 206/320 |
| 4,866,215 | 9/1989 | Muller et al. | 174/50 |
| 4,895,161 | 1/1990 | Cudahy et al. | 128/630 |
| 5,080,228 | 1/1992 | Maston, III et al. | 206/328 |
| 5,134,546 | 7/1992 | Izumi et al. | 361/395 |
| 5,144,657 | 9/1992 | Depaepe | 379/438 |
| 5,187,766 | 2/1993 | Finzel et al. | 206/316.1 |

FOREIGN PATENT DOCUMENTS

| | | |
|---|---|---|
| 340444 | 3/1989 | European Pat. Off. . |
| 6948919 | 12/1969 | Germany . |
| 7506668 | 3/1975 | Germany . |
| 3542871 | 4/1985 | Germany . |

Primary Examiner—Randall L. Green
Assistant Examiner—P. Zuttarelli
Attorney, Agent, or Firm—Woodcock Washburn Kurtz Mackiewicz & Norris

[57] ABSTRACT

A medical monitor (1) comprises a recess (6) in its bottom side. A lateral wall (9) of this recess (6) is oriented in the same direction as the front panel (2) of medical monitor (1) and carries connectors or jacks. If the medical monitor is operated in a vertical position, its rear panel becomes its top panel. The rear panel does not comprise any connectors, and the connectors at lateral wall (9) as well as patient connectors (3a, 3b, 3c, 4) are oriented downwards. Therefore, the monitor is safe against sprayed or spilled fluids even if operated in vertical position.

18 Claims, 2 Drawing Sheets

MEDICAL MONITOR

This is a continuation, of application Ser. No. 07/767,240, filed Sep. 27, 1991 now abandoned.

FIELD OF THE INVENTION

The present invention generally relates to a medical monitor, e.g., a fetal monitor, and particularly relates to a casing for a medical monitor.

BACKGROUND OF THE INVENTION

Medical monitors are used in a variety of clinical applications, e.g., in the operating room, in the anesthesia or recovery room, in the intensive care unit or in the delivery room. They are, for example, used to monitor the electrocardiogram, respiration, body temperature, various blood gases, and so on, of a patient in order to carry out a clinically meaningful evaluation of the patient's condition. Monitors of this type usually comprise a box or casing containing the printed circuit boards with the electronic circuitry necessary to process, filter, etc., the physiological signals received from a sensor or transducer connected with the medical monitor. The output is then either displayed in numerical form or as a wave, e.g., on a cathode ray tube (CRT) or a 7-segment display. In addition, or as an alternative, the output may also be recorded on a printer and/or fed to a central station or the like.

For the purpose of interconnection with a central station, other monitors, recorders, etc., most medical monitors are additionally equipped with jacks located at the rear panel of the casing. Examples of such connectors are:

a) a digital system connector, i.e., a connector for exchanging digital data indicative of patient waves, trends, alarm messages, etc., with a central station;

b) a digital or analog output for feeding signals, waves, etc., to another monitor for display, or to a recorder;

c) digital or analog inputs, e.g., for receiving signals from another device, for the purpose of displaying, printing or recording;

d) an output for feeding digital or analog signals to a slave display or via communication lines—such as a telephone link—to a remote place, e.g., the physician's home.

The above list contains only some examples of situations where a connection of a medical monitor with another device is necessary. Other kinds of connections may be required as well.

A specific embodiment of the present invention relates to a fetal monitor. A fetal monitor measures and records the fetal beat-to-beat heart rate (FHR) and the uterus activity (toco) simultaneously, which allows an exact determination of the fetal condition. The fetal beat-to-beat heart rate may be obtained from an electrocardiogram signal, e.g., via a spiral electrode screwed into the fetal epidermis, or by the Doppler shift of an ultrasound signal (the moving parts of the fetal heart, i.e., its valves and walls, cause a Doppler shift in the reflected ultrasound wave). The maternal electrocardiogram may be recorded as well. Although the specific embodiment described herein is a fetal monitor (in fact, the present invention was made during the design process of such a fetal monitor), the invention may also be applied to other kinds of instruments.

The lack of available space for all kinds of monitoring devices presents a serious problem in both hospitals and the private practices of physicians. There are several clinical applications, e.g., the operating room, where multiple physiological parameters of a patient must be monitored. Efforts have already been made to combine several medical monitoring devices in multi-parameter monitors or to incorporate various monitors in a cabinet. In the private practice of a physician, this usually does not help; although only one or very few medical parameters are recorded there, the available space is considerably less than in a hospital. This is particularly true in the case of an antepartum monitor, i.e., a fetal monitor used for screening measurements during gestation. However, even in hospital applications, the solutions of a cabinet or a combined monitor are not always adequate.

A basic goal of the inventor of the present invention is to provide a medical monitor which can be operated in both a horizontal position, as usual, and also in a vertical position. It would thus become possible to use the medical monitor on a desk, a shelf, etc., and also to hang it on a wall or the like and operate it from there. This would not only save considerable space, but would also be useful in placing the monitor close to a patient's bed.

The feature of vertical operation would be particularly suited for monitors which are light or have a relatively flat casing. Furthermore, it would be of particular value for monitors without a bulky CRT, although even monitors with a CRT could be operated in the vertical position.

If operated in a vertical position, the medical monitor could be hung up on a wall in any convenient manner, e.g., using hooks, screws or the like.

When designing a medical monitor, e.g., a fetal monitor, for operation in a vertical position, a problem encountered in a hospital or medical environment in general is that the monitor must be resistant to the spray of water and disinfection fluids as well as spillage of these and other fluids. The operation of the monitor must not be impaired when a fluid is spilled over the monitor. In industrial practice, the required safety of the monitor is therefore usually tested in a "spillage test."

The requirement outlined above cannot be fulfilled if the connector jacks of the medical monitor are, as is usual in the art, placed on the rear panel of the monitor, as the rear panel becomes the upper panel in the vertical position. The same is true for the power inlet. If one of these jacks were placed at the rear panel, i.e., the upper panel in the vertical position, a fluid spilled over the monitor would penetrate into its casing, causing the monitor to malfunction.

It is therefore a major objective of the present invention to provide a medical monitor which may be operated in a horizontal position and also in a vertical position, whereby safe operation is particularly ensured in the vertical position when a fluid is spilled or sprayed over the monitor.

SUMMARY OF THE INVENTION

The invention encompasses casings for an instrument such as a medical monitor or other similar device, and medical monitors. In accordance with the foregoing objectives, a casing for a medical monitor in accordance with the present invention comprises a front panel and a bottom side comprising a recess with at least three lateral walls at least one of which is substantially parallel to and located opposite the front panel. One of the lateral walls comprises means for connecting at least one cable.

In a preferred embodiment of the present invention the bottom side comprises, outside the recess, at least three base support plugs.

In another embodiment of the present invention the bottom side comprises a second recess arranged between and connecting one of the lateral walls and a rear panel.

In still another embodiment the second recess comprises a strain relieving device.

In one embodiment the strain relieving device comprises at least a tongue protruding from a side wall of the second recess.

In a further embodiment the tongue is made of elastic material.

In addition, the tongue may be pivoted in the casing and the casing may further comprise spring means for forcing the tongue to a closed position.

In still yet another embodiment the casing further comprises a torus-like shoulder extending around the casing in a direction parallel to the front panel and including a side wall a part of which adjoins the recess and forms one of the lateral walls.

In still another embodiment of the invention the front panel comprises means for connecting a patient cable.

In still yet another embodiment the casing comprises a power inlet jack.

The present invention also encompasses medical monitors comprising a casing containing electronic circuitry for receiving, processing, displaying and/or recording signals representative of physiological parameters of a subject. The casing of medical monitors in accordance with the invention comprises a front panel, a bottom side comprising a recess with at least three lateral walls, at least one of the lateral walls arranged substantially parallel to and opposite the front panel so that its surface is basically oriented in the same direction as the front panel. The said one of the lateral walls comprises at least one jack or connector for connection of an interface cable.

In a preferred embodiment of a medical monitor in accordance with the present invention the recess at the bottom side of the casing is rectangular, with its edges being substantially parallel to the outer edges of the monitor. However, other suitable geometric shapes, such as a triangle or a polygon, may be used.

Such a recess comprises several surfaces. One is, of course, the bottom surface, i.e., a plane substantially parallel to the bottom surface of the monitor. The other surfaces are lateral or side walls which are substantially parallel to or inclined with respect to the side walls of the monitor.

At least one of the lateral walls is substantially parallel to and located opposite the front panel. That is, the normal on the specific lateral wall points basically in the same direction as the normal on the front panel. It may also be inclined with respect to the front panel. The wording "basically in the same direction" as used herein is intended to cover the exactly parallel case as well as the inclined configuration. In the case of a rectangular configuration, the said one of the lateral walls is opposite to the wall in the recess adjoining or nearest to the front panel.

The said one of the lateral walls carries the connectors and/or jacks for connection of the medical monitor to other devices, such as system connectors, digital or analog inputs and outputs, etc. It may, however, also carry the connectors and/or jacks for connection of interface cables and also the connectors/jacks necessary for connection of a sensor or transducer, or for power. Moreover, there are other advantageous ways of positioning the power inlet and the patient connectors, e.g., the power inlet may be positioned on a side wall of the casing and the patient connectors may be positioned on the front panel.

Therefore, the rear panel of the medical monitor, which becomes the upper panel when the monitor is operated in the vertical position, need not carry connectors or jacks. (However, a jack for connecting the patient to earth, which cannot cause malfunction of the monitor, may still be placed on the rear panel). On the other hand, the connectors or jacks positioned on the said one of the lateral walls in the recess are oriented downwards when the monitor is operated in its vertical position. Therefore no sprayed or spilled fluid may penetrate into the opening constituted by any connector or jack, so that the medical monitor becomes fluid-proof. It may therefore be operated in the horizontal as well as in the vertical position, even in a medical environment.

If, as proposed herein, the jacks are placed on a lateral wall of a recess on the bottom side of the medical monitor, the connectors of the interface cables or the like are contained, if connected, in the recess. In order to feed the cables to the outside, particularly if the monitor is operated in its horizontal position, various solutions are possible. In a preferred embodiment, the bottom side of the casing comprises, outside the recess, at least three, but preferably four, base support plugs or studs. This makes it easy to feed the interface cables to the outside using the space between the monitor and its support.

In another preferred embodiment, the bottom side of the casing comprises a second recess arranged between and connecting one of the said lateral walls and the rear panel of the casing. This feature makes it possible to feed the interface cables to the rear side of the medical monitor while being kept in the second recess. This is important in order to keep the cables away from the person operating the monitor, or to reduce the number of visible cables leading to the monitor. Last but not least, keeping the interface cables out of sight improves the appearance of the whole unit.

The second recess may advantageously comprise a strain relieving device. This will ensure that the interface cables are kept reliably in the second recess, particularly if the monitor is operated in its horizontal position. It will also ensure that mechanical stress won't cause damage to any of the connections. Preferably, the strain relieving device will comprise at least one tongue protruding from a side wall of the second recess, in particular a resilient tongue made of an elastic material such as plastic. The distance between the tongue and the bottom of the second recess will preferably be slightly smaller than the diameter of an interface cable, so that cables pushed between the bottom of the second recess and the tongue will be kept in position. The tongue may also comprise an additional nose that prevents the interface cables from sliding out of their position between the tongue and the bottom of the second recess.

In an alternate embodiment, the tongue may be hinged to the casing of the monitor, i.e., attached to the casing, whereby spring means force the tongue to its closed position. The spring means may be any suitable spring known in the art, for example, a leg spring or a spring clip.

In an advantageous and preferred embodiment, the medical monitor comprises a torus-like shoulder basically extending around the casing in a parallel direction to the front panel, such that a part of a side wall of the torus-like shoulder adjoins the recess and forms one of the lateral walls. The torus-like shoulder carries the displays, push buttons, etc., necessary to operate the monitor. As it joins the first recess, its side wall is identical with the lateral wall of the first recess located opposite to the front panel. Therefore, this lateral wall is of greater depth than the other lateral walls. A particular advantage of this design is that, due to the increased depth, the available space for placing connectors or jacks is increased. In other words, the first recess may be of a limited depth, whereas the remaining space on this lateral wall is still sufficient to accommodate several jacks or connectors. In case such torus-like shoulder is provided, it may further be advantageous to form the second recess in the shoulder. Although the torus-like shoulder preferably surrounds the medical monitor, i.e., extends around the whole casing, it will be understood that this is not a necessary condition.

Other features and advantages of the invention can be found in the claims and in the detailed description.

DETAILED DESCRIPTION OF A PREFERRED EMBODIMENT

The invention will now be explained by means of a non-limiting example with reference to the accompanying drawings.

Figure 1:
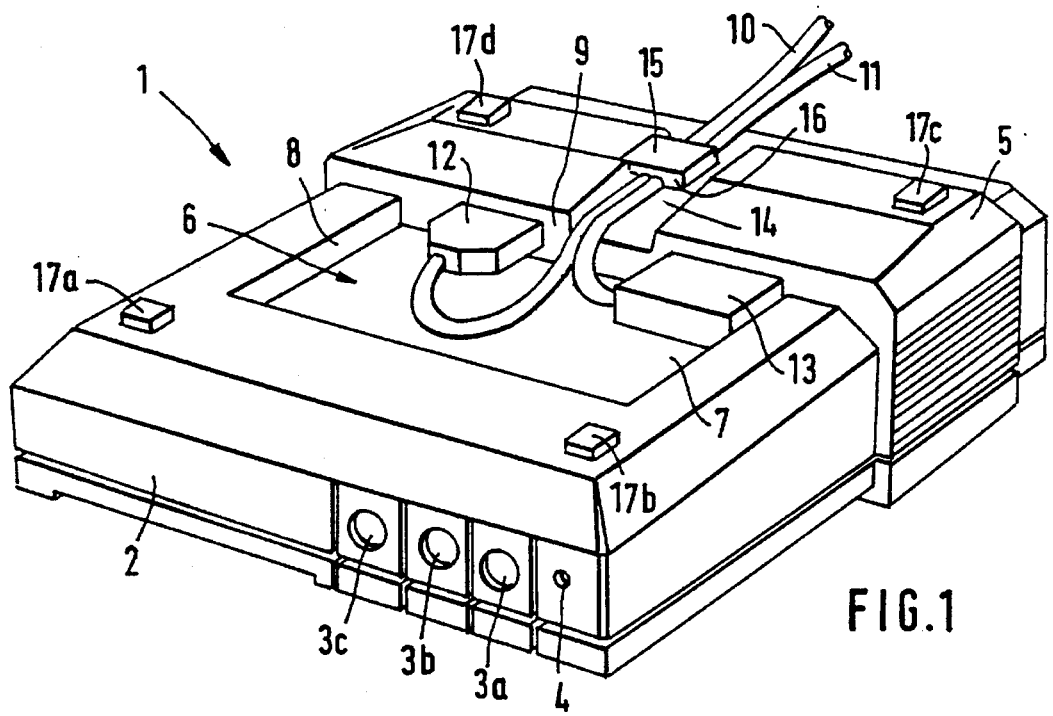
FIG. 1 is a bottom view of a medical monitor according to the invention.

FIG. 1 depicts the bottom view of a fetal monitor 1 (which is an antepartum monitor). A front panel 2 carries a connector 3a for connection of an ultrasound transducer used to determine the fetal beat-to-beat heart rate. Connector 3b is provided for a toco (labor activity) transducer, and connector 3c is provided for a signal obtained from a second fetus (in case that twins are to be monitored). A fourth jack 4 is provided for connection of an external event marking device.

The casing of fetal monitor 1 further comprises a torus-like shoulder 5 extending around the casing and manufactured as an integral part of the casing. A recess 6 of rectangular shape is formed in the bottom of the monitor. It comprises a bottom surface or wall 7 and four lateral or side walls, two of which are visible in FIG. 1 and labelled as 8 and 9. The lateral wall next to front panel 2 is inclined (not shown in FIG. 1).

Lateral wall 9 is parallel to front panel 2 and located opposite to it, i.e., faces the same direction as front panel 2. Its depth is greater than the depth of lateral wall 8, as it is also part of torus-like shoulder 5.

Lateral wall 9 further carries two jacks or connectors for connection of two interface cables 10 and 11, which in turn are equipped with connectors 12 and 13. Interface cables 10 and 11 are fed through a second recess 14 formed in torus-like shoulder 5. A tongue 15 is either pivoted in the casing or made of elastic material and keeps cables 10 and 11 in place. A nose 16 prevents the cables from sliding away.

The bottom side of monitor 1 comprises further, outside of recess 6, four support plugs or studs 17a to 17d.

Figure 2:
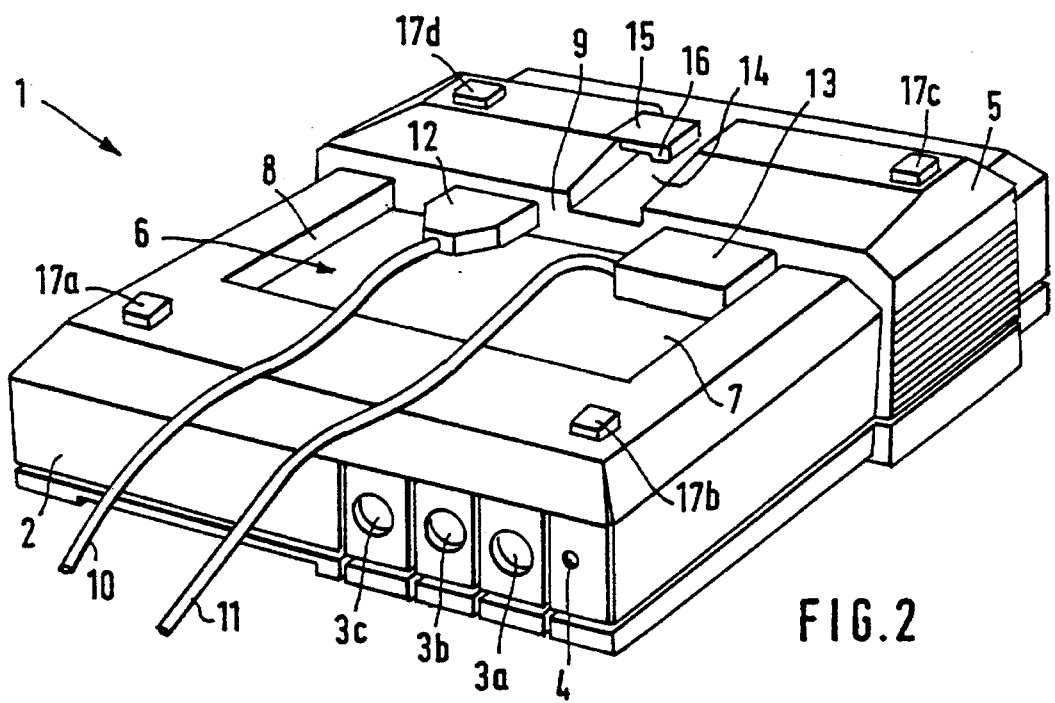
FIG. 2 is a bottom view with a different arrangement of the interface cables.

In operation, interface cables 10 and 11 are either fed to the rear side of fetal monitor 1, as shown in FIG. 1, or to its front side, as shown in FIG. 2. The plugs or studs 17a to 17d ensure, in the environment of FIG. 2, that the interface cables may be fed through the space between the fetal monitor and its support.

Figure 3:
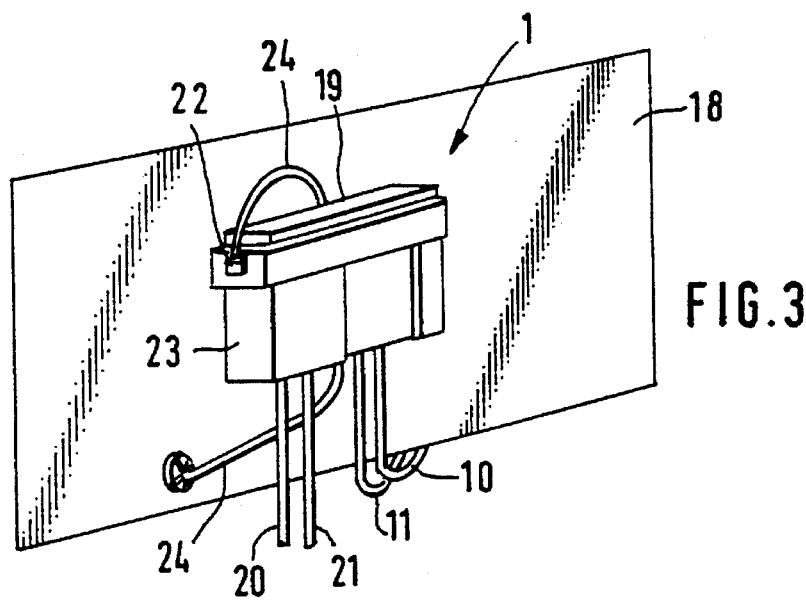
FIG. 3 depicts the medical monitor operated in vertical position.

FIG. 3 depicts fetal monitor 1 operated in a vertical position. The monitor is fastened to a wall 18 in any convenient manner, e.g., using hooks, screws or the like. In this position rear panel 19 of the monitor becomes its top panel. As this panel does not carry any jacks or connectors, and as the interface connectors are directed downwards, the monitor is protected against sprayed or spilled fluids.

The interface cables 10 and 11 extend in the direction of the front panel, as depicted in FIG. 2. Furthermore, two patient cables 20 and 21 are connected. The jacks for these cables are also oriented downwards, so that no fluids may penetrate into the monitor. A power inlet 22 is arranged on a side wall 23 of the monitor and a power cable 24 fed through recess 14 (FIGS. 1, 2) is connected via the power inlet.

Figure 4:
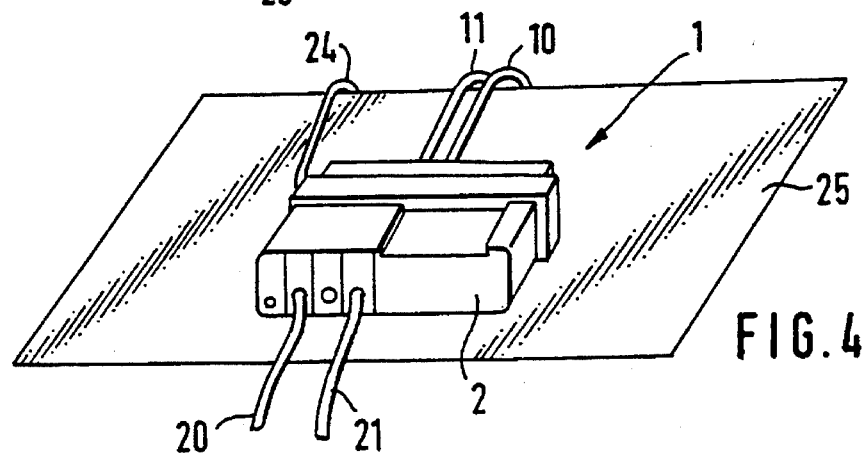
FIG. 4 depicts the monitor in its horizontal position.

FIG. 4 depicts fetal monitor 1 operated in its horizontal position. The monitor is placed on a horizontal support (e.g., a table) 25, wherein the torus-like shoulder 5 causes a slight inclination or tilt of the monitor, so that operation of the keys and reading of the displays (arranged on the top of the torus-like shoulder, but not shown in FIG. 4) becomes easier. The arrangement of interface cables 10 and 11 is the same as in FIG. 1, i.e., the interface cables are fed to the rear of the monitor. The monitor is also protected against fluids in this horizontal position.

Figure 5:
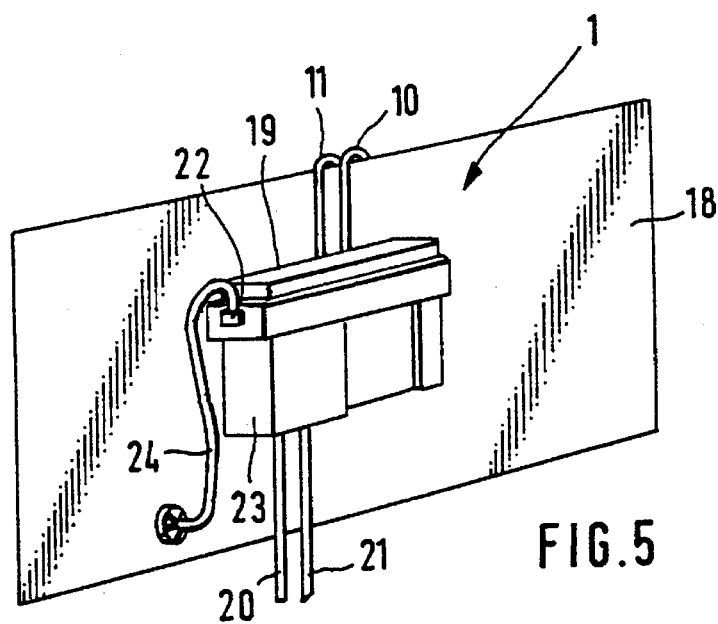
FIG. 5 is another example of the vertical operating position, with the cables being fed in a different manner.

A further example, again with the monitor in the vertical position, is depicted in FIG. 5. Interface cables 10 and 11 are, in this environment, arranged as in FIG. 1, i.e., the interface cables are fed to the rear side of fetal monitor 1.

Although specific embodiments of the invention have been described, the true scope of the invention, as recited in the following claims, is not limited to those embodiments. For example, the invention is not intended to be limited to a fetal monitor or even to a medical monitor, as the principles described above may be advantageously applied to other types of electronic instruments as well.

What is claimed is:

1. A casing for an instrument, comprising:

a front panel characterized by a first normal vector, said first normal vector being defined as a vector oriented in a direction which is normal to a surface of said front panel;

a bottom side, attached to said front panel, comprising a recess, said recess comprising at least three lateral walls at least one of which is substantially parallel to and located opposite said front panel, wherein an outside surface of said at least one of said lateral walls is characterized by a second normal vector that is defined as a vector oriented in a direction which is normal to said outside surface, said second normal vector being oriented in substantially the same direction as said first normal vector of the front panel, and said at least one of said lateral walls comprises at least one cable connector;

means for hanging the casing substantially vertically such that said first and second normal vectors are oriented substantially in a downward direction; and a shoulder extending around said casing in a direction parallel to said front panel and including a side wall a part of which adjoins said recess and forms said at least one of said lateral walls.

2. A casing as recited in claim 1, further comprising a second recess arranged between and connecting said at least one of said lateral walls and a rear panel.

3. A casing as recited in claim 1, wherein said front panel comprises means for connecting a patient cable.

4. A casing as recited in claim 1, further comprising a power inlet jack.

5. A casing as recited in claim 1, wherein said bottom side comprises, outside said recess, at least three base support plugs.

6. A casing as recited in claim 1 or 5, wherein said bottom side comprises a second recess arranged between and connecting said at least one of said lateral walls and a rear panel.

7. A casing as recited in claim 6, wherein said second recess comprises a strain relieving device.

8. A casing as recited in claim 7, wherein said strain relieving device comprises at least a tongue protruding from a side wall of said second recess.

9. A casing as recited in claim 8, wherein said tongue is made of elastic material.

10. A casing as recited in claim 8, wherein said tongue is pivoted in said casing and further comprising spring means for forcing said tongue to a closed position.

11. A medical monitor, comprising:

a casing containing electronic circuitry for receiving, processing, displaying and recording signals representative of physiological parameters of a subject, said casing comprising:

a front panel characterized by a first normal vector, said first normal vector being defined as a vector oriented in a direction which is normal to a surface of said front panel;

a bottom side, attached to said front panel, comprising a recess, said recess comprising at least three lateral walls at least one of which is substantially parallel to and located opposite said front panel, wherein an outside surface of said at least one of said lateral walls is characterized by a second normal vector that is defined as a vector oriented in a direction which is normal to said outside surface, said second normal vector being oriented in substantially the same direction as said first normal vector of the front panel, and said at least one of said lateral walls comprises at least one jack or connector for connection of an interface cable; and means for hanging the casing substantially vertically such that said first and second normal vectors are oriented substantially in a downward direction; and a shoulder extending around said casing in a direction parallel to said front panel and including a side wall a part of which adjoins said recess and forms said at least one of said lateral walls.

12. A medical monitor as recited in claim 11, further comprising a second recess arranged between and connecting said at least one of said lateral walls and a rear panel.

13. A medical monitor as recited in claim 11, wherein said front panel comprises means for connecting a patient cable.

14. A medical monitor as recited in claim 11, wherein said bottom side comprises a second recess arranged between and connecting said at least one of said lateral walls and a rear panel.

15. A medical monitor as recited in claim 14, wherein said second recess comprises a strain relieving device.

16. A medical monitor as recited in claim 15, wherein said strain relieving device comprises at least a tongue protruding from a side wall of said second recess.

17. A medical monitor as recited in claim 16, wherein said tongue is made of elastic material.

18. A medical monitor as recited in claim 16, wherein said tongue is pivoted in said casing and further comprising spring means for forcing said tongue to a closed position.

* * * * *